(12) United States Patent
Guo et al.

(10) Patent No.: US 9,234,179 B2
(45) Date of Patent: Jan. 12, 2016

(54) MATERIALS AND METHODS FOR GENERATING PLURIPOTENT STEM CELLS

(75) Inventors: Lihe Guo, Shanghai (CN); Tianjin Liu, Shanghai (CN)

(73) Assignees: SHANGHAI ICELL BIOTECHNOLOGY CO., LTD. (CN); SHANGHAI UNITED STEM CELL BIOTECHNOLOGY CO., LTD. (CN)

( * ) Notice: Subject to any disclaimer, the term of this patent is extended or adjusted under 35 U.S.C. 154(b) by 709 days.

(21) Appl. No.: 13/516,530

(22) PCT Filed: Dec. 18, 2009

(86) PCT No.: PCT/CN2009/075733
§ 371 (c)(1),
(2), (4) Date: Jun. 15, 2012

(87) PCT Pub. No.: WO2011/072461
PCT Pub. Date: Jun. 23, 2011

(65) Prior Publication Data
US 2012/0269782 A1 Oct. 25, 2012

(51) Int. Cl.
*C12N 5/02* (2006.01)
*C12N 5/00* (2006.01)
*C12N 5/08* (2006.01)
*A01N 63/00* (2006.01)
*C12N 5/074* (2010.01)
*C12N 5/071* (2010.01)
*C12N 5/0735* (2010.01)
*C12N 5/07* (2010.01)

(52) U.S. Cl.
CPC ............... *C12N 5/0696* (2013.01); *C12N 5/06* (2013.01); *C12N 5/0606* (2013.01); *C12N 5/0625* (2013.01); *C12N 2500/84* (2013.01); *C12N 2501/115* (2013.01); *C12N 2501/235* (2013.01); *C12N 2502/025* (2013.01); *C12N 2506/09* (2013.01); *C12N 2506/13* (2013.01); *C12N 2506/1307* (2013.01)

(58) Field of Classification Search
CPC ...... C12N 5/06; C12N 5/0606; C12N 5/0625; C12N 5/0696; C12N 2501/115; C12N 2501/235; C12N 2502/025; C12N 2506/09; C12N 2506/1307
USPC ........................... 424/93.7; 435/325, 371, 377
See application file for complete search history.

(56) References Cited

U.S. PATENT DOCUMENTS

| | | | |
|---|---|---|---|
| 5,578,475 A | 11/1996 | Jessee | |
| 5,843,780 A | 12/1998 | Thomson | |
| 5,919,449 A | 7/1999 | Dinsmore | |
| 5,968,829 A | 10/1999 | Carpenter | |
| 6,020,202 A | 2/2000 | Jessee | |
| 6,051,429 A | 4/2000 | Hawley-Nelson et al. | |
| 6,090,622 A | 7/2000 | Gearhart et al. | |

FOREIGN PATENT DOCUMENTS

| | | |
|---|---|---|
| WO | 99/03973 A1 | 1/1999 |
| WO | 2008002329 A2 | 1/2008 |

OTHER PUBLICATIONS

Sugii et al., 2012, US 20120263689 A1, effective filing date Sep. 10, 2009.*
Lai et al., 2012, US 20120122213 A1, effective filing date, May 5, 2009.*
Kolf et al., 2007, Arthritis Research & Therapy, vol. 9, p. 204, 10 pages.*
Alenzi et al., 2011, African Journal of Biotechnology, vol. 10(86), pp. 19929-19940.*
Bellin et al., 2012, Nature reviews/Molecular Cell Biology, vol. 13, p. 713-726.*
Office Action of Japanese application No. JP2012543441 issued Feb 2, 2015; with partial translation; 4 pages.
Office Action of Japanese application No. JP2012543441 issued Jun. 4, 2014; with partial translation; 6 pages.
European Examination Report for European Application No. 09852199.0, Date Jan. 23, 2015, 3 pages.
Office Action of Chinese Application No. 200980162975.1; Issued on Feb. 5, 2013, (including partial translation), 5 pages.
Abuyumeko; "Regenerative Medical Treatment Performed Using Amnions" Obstetrics and Gynecology (Japanese); 2009; vol. 10; No. 65; pp. 1233-1237 (English Translation).
European Application No. 09852199; Examination Report dated Nov. 12, 2013, 4 pgs.
Morio Ueno et al.; "Neural conversion of ES cells by an inductive activity on human amniotic membrane matrix"; Proc. Natl. Acad. Sci,. USA; Jun. 2006; vol. 103; No. 25; pp. 9554-9559.
Raymond M. Anchan et al.; "Amniocytes can serve a dual function as a source of iPS cells and feeder layers"; Human Molecular Genetics; 2011; vol. 20; No. 5; pp. 962-974.
Shogo Nagata et al.; "Efficient reprogramming of human and mouse primary extra-embryonic cells to pluripotent stem cells"; Genes to Cells; 2009; vol. 14; pp. 1395-1404.
Dabeva, M.D. et al., Activation, proliferation, and differentiation of progenitor cells into hepatocytes in the D-galactosamine model of liver regeneration, Am J Pathol. 1993; 143(6): 1606-1620.
International Search Report for PCT CN2009/075733 dated Aug. 26, 2010.
Kim, J.H. et al., Dopamine neurons derived from embryonic stem cells function in an animal model of Parkinson's disease, Nature, 2002;418 (6893): 50-56. Epub Jun. 20, 2002.
Li, R-K et al., Cardiomyocyte transplantation improves heart function, Ann Thorac Surg. 1996; 62(3):654-660.

(Continued)

*Primary Examiner* — Shin Lin Chen
(74) *Attorney, Agent, or Firm* — Cantor Colburn LLP

(57) ABSTRACT

The present invention relates to a method of reprogramming a somatic cell to produce an induced pluripotent stem (iPS) cell which is capable of differentiating into somatic cells derived from ectoderm, mesoderm or endoderm. The present invention also relates to the aforementioned iPS cells, methods of generating and maintaining iPS cells, and methods of using iPS cells.

7 Claims, 10 Drawing Sheets

(56) References Cited

OTHER PUBLICATIONS

Maherali, N. et al., Directly reprogrammed fibroblasts show global epigenetic remodeling and widespread tissue contribution, Cell Stem Cell. 2007;1(1): 55-70.
McDonald, J.W. et al., Transplanted embryonic stem cells survive, differentiate and promote recovery in injured rat spinal cord, Nat Med. 1999; 5(12):1410-1412.
Min, J-Y et al., Transplantation of embryonic stem cells improves cardiac function in postinfarcted rats, J Appl Physiol. 2002; 92(1):288-296.
Nakagawa, M. et al., Generation of induced pluripotent stem cells without Myc from mouse and human fibroblasts, Nat Biotechnol. 2008; 26(1):101-106. Epub Nov. 30, 2007.
Okita, K. et al., Generation of germline-competent induced pluripotent stem cells, Nature. 2007; 448(7151): 313-317. Epub Jun. 6, 2007.
Park, I-H et al., Reprogramming of human somatic cells to pluripotency with defined factors, Nature, 2008;451(7175):141-146. Epub Dec. 23, 2007.
Sakai, T. et al., Autologous heart cell transplantation improves cardiac function after myocardial injury, Ann Thorac Surg 1999; 68:2074-2080.
Sakai, T. et al., Fetal cell transplantation: a comparison of three cell types, J Thorac Cardiovasc Surg. 1999;118(4):715-724.
Shamblott, M.J. et al., Derivation of pluripotent stem cells from cultured human primordial germ cells, Proc Natl Acad Sci U S A. 1998; 95(23):13726-13731.
Takahashi, K. et al., Induction of Pluripotent Stem Cells from Mouse Embryonic and Adult Fibroblast Cultures by Defined Factors, Cell. 2006;126(4):663-676. Epub Aug. 10, 2006.
Takahashi, K. et al., Induction of Pluripotent Stem Cells from Adult Human Fibroblasts by Defined Factors, Cell. 2007;131(5):861-872.
Thomson, J.A. et al., Isolation of a primate embryonic stem cell line, Proc Natl Acad Sci U S A. 1995; 92(17): 7844-7848.
Thomson, J.A. et al., Embryonic Stem Cell Lines Derived from Human Blastocysts, Science. 1998; 282(5391):1145-1147.
Wernig, M. et al., In vitro reprogramming of fibroblasts into a pluripotent ES-cell-like state, Nature, 2007; 448(7151):318-324. Epub Jun. 6, 2007.
Wernig, M. et al., Neurons derived from reprogrammed fibroblasts functionally integrate into the fetal brain and improve symptoms of rats with Parkinson's disease, Proc Natl Acad Sci U S A. 2008;105(15): 5856-5861. Epub Apr. 7, 2008.
Ye, L. et al., Induced pluripotent stem cells offer new approach to therapy in thalassemia and sickle cell anemia and option in prenatal diagnosis in genetic diseases, Proc Natl Acad Sci U S A. 2009; 106(24): 9826-9830.
Yu, J. et al., Induced Pluripotent Stem Cell Lines Derived from Human Somatic Cells, Science, 2007; 318 (5858):1917-1920. Epub Nov. 20, 2007.
European Search Report; European Application No. 09852199; Jun. 28, 2013, 7 pgs.
Hanna, J. et al., "Treatment of Sickle Cell Anemia Mouse Model with iPS Cell Generated from Autologous Skin", Science, American Asociation for the Advancement of Sicence, vol. 318, No. 5858, Dec. 21, 2007, pp. 1920-1923.
Miyamoto, K. et al.; "Human Placenta Feeder Layers Support Undifferentiated Growth of Primate Embryonic Stem Cells", Stem Cells, Alphmed Press, vol. 22, No. 4, Jan. 1, 2004, pp. 433-440.
Yam, H-F et al.; "Growth Factor Changes in Ex Vivo Expansion of Human Limbal Epithelial Cells on Human Amniotic Membrane", Cornea, vol. 21, No. 1, 2002, pp. 101-105.
Yu, J. et al.; "Human Induced Pluripotent Stem Cells Free of Vector and Transgene Sequences", Science, May 8, 2009, vol. 32, pp. 797-801.
International Preliminary Report on Patentability for PCT/CN2009/075733 issued on Jun. 19, 2012.

\* cited by examiner

Nanog        OCT-4        c-MYC

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gaggagtccc aggacatgaa                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gtggtctggc tgaacacctt                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gccgagtgga aactttgtc                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
gttcatgtgc gcgtaactgt                                                 20

<210> SEQ ID NO 5
<211> LENGTH: 23
<212> TYPE: DNA
<213> ORGANISM: Artificial Sequence
<220> FEATURE:
<223> OTHER INFORMATION: Synthetic primer

<400> SEQUENCE: 5
gcgtacgcaa attaaagtcc aga                                             23

<210> SEQ ID NO 6
<211> LENGTH: 25
<212> TYPE: DNA
<213> ORGANISM: Artificial Sequence
<220> FEATURE:
<223> OTHER INFORMATION: Synthetic primer
```

-continued

<400> SEQUENCE: 6
cagcatccta aacagctcgc agaat                                        25

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
agagtgtctg gagcaagttg c                                            21

<210> SEQ ID NO 8
<211> LENGTH: 21
<212> TYPE: DNA
<213> ORGANISM: Artificial sequence
<220> FEATURE:
<223> OTHER INFORMATION: Synthetic primer

<400> SEQUENCE: 8
cgtagtccat gttcacaatc g                                            21

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
ctcagcctcc agcagatgc                                               19

<210> SEQ ID NO 10
<211> LENGTH: 17
<212> TYPE: DNA
<213> ORGANISM: Artificial Sequence
<220> FEATURE:
<223> OTHER INFORMATION: Synthetic primer

<400> SEQUENCE: 10
ccttctgcgt cacactg                                                 17

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
ccccagccct ctcctcccca ata                                          23

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
tgccccccac cctcccacag tag                                          23

<210> SEQ ID NO 13

```
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
ggacctggaa tatggcgaga aa                                              22

<210> SEQ ID NO 14
<211> LENGTH: 26
<212> TYPE: DNA
<213> ORGANISM: Artificial Sequence
<220> FEATURE:
<223> OTHER INFORMATION: Synthetic primer

<400> SEQUENCE: 14
tgatatacac tgttctacaa atcccg                                          26
```

MATERIALS AND METHODS FOR GENERATING PLURIPOTENT STEM CELLS

CROSS-REFERENCE TO RELATED APPLICATIONS

This application is the US National Stage Application of International Application No. PCT/CN2009/075733, filed Dec. 18, 2009.

TECHNICAL FIELD

This invention relates generally to the field of cell biology. More specifically, it relates to the propagation of pluripotent stem cells, and culture conditions and materials that facilitate propagation and use of stem cells.

BACKGROUND

The following description is provided to assist the understanding of the reader. None of the information provided or references cited is admitted to be prior art to the present invention.

Stem cells are cells having the ability to self-renew and divide to an unlimited extent and to differentiate under suitable circumstances to form different types of cells. Embryonic stem cells (ES cells) are stem cells established from early embryos which can be cultured over a long period of time while maintaining pluripotent ability to differentiate into all kinds of cells existing in living bodies. By contrast, somatic stem cells are any cell which is found in a developed organism that has the ability to divide and create another cell like itself and also divide and create a cell more differentiated than itself.

Thomson et al. (U.S. Pat. No. 5,843,780; *Proc. Natl. Acad. Sci. USA* 92:7844, 1995) were the first to successfully isolate and propagate pluripotent stem cells from primates. They subsequently derived human embryonic stem (hES) cell lines from human blastocysts (*Science* 282:114, 1998). Gearhart and coworkers derived human embryonic germ (hEG) cell lines from fetal gonadal tissue (Shamblott et al., *Proc. Natl. Acad. Sci. USA* 95:13726, 1998; and U.S. Pat. No. 6,090,622). Both hES and hEG cells have the long-sought characteristics of pluripotent stem cells, i.e., they can be cultured extensively without differentiating, they have a normal karyotype, and they remain capable of producing a number of important cell types.

Induced pluripotent stem (iPS) cells are a type of pluripotent stem cell artificially derived from a non-pluripotent cell, typically an adult somatic cell. Yamanaka et al. transfected mouse fibroblasts with four genes (Oct4, Sox2, c-Myc, Klf4) to obtain iPS cells in 2006. Subsequently, iPS cells were created from human adult somatic cells. (Takahashi et al. *Cell*, 131:861-872 (2007); Yu et al. *Science*, 318:1917-1920, 2007).

The field of regenerative medicine encompasses therapies designed to aid the repair, replacement, or regeneration of damaged cells, tissues, or organs. Stem cell-based therapies have the promise of treating a variety of health conditions including Alzheimer's Disease, Parkinson's Disease, stroke, spinal injuries, heart attack, renal failure, osteoporosis, type I diabetes, multiple sclerosis, rheumatoid arthritis, burns, and wounds. However, the progress of such therapies has been hindered by a range of factors including the possibility of immune rejection of ES cells derived from a donor who is immunologically incompatible with the recipient.

SUMMARY

This invention relates generally to methods for generating stem cells. In one aspect, the present disclosure provides a method for obtaining an induced pluripotent stem cell comprising culturing one or more somatic cells on a feeder layer of amniotic epithelial cells. In one embodiment, the amniotic epithelial cells are mammalian amniotic epithelial cells. In one embodiment, the mammalian amniotic epithelial cells are derived from a mammal selected from the group consisting of: human, pig, dog, horse, cattle, sheep, and rodents, such as rat and mouse. In one embodiment, the amniotic epithelial cells are human amniotic epithelial cells. In one embodiment, the amniotic epithelial cells have been cultured for fewer than 6 serial passages ($P_0$-$P_5$). In one embodiment, the amniotic epithelial cells are newly isolated $P_0$ amniotic epithelial cells.

In one embodiment, the somatic cells are selected from the group consisting of: adult skin fibroblast (ADSF) cells, human embryonic fibroblast (HEF) cells, mouse fibroblast (MF) cells, mouse embryonic fibroblast (MEF) cells, pig fibroblast (PF) cells, and pig embryonic fibroblast (PEF) cells. In one embodiment, the somatic cells are adult skin fibroblast (ADSF) cells.

In one embodiment, the cells are cultured in KO-DMEM medium. In one embodiment, the KO-DMEM medium comprises bFGF, human umbilical serum, and LIF.

In an illustrative embodiment, the KO-DMEM comprises 10 ng/ml bFGF, 5% human umbilical serum, newborn bovine serum, fetal bovine serum and 12 ng/ml LIF.

In one aspect, the present disclosure provides an induced pluripotent stem cell obtained by the method describe above. In one aspect, the present disclosure provides a somatic cell derived by inducing differentiation of the pluripotent stem cell.

In one aspect, the present disclosure provides a method for stem cell therapy comprising: (a) isolating and collecting a somatic cell from a subject, i.e., a human or animal; (b) reprogramming the somatic cell into a pluripotent stem cell; (c) inducing differentiation of the pluripotent stem cell; and (d) transplanting the differentiated cell from (c) into the subject. In some embodiments, the stem cell therapy may be used for regenerative medicine, tissue engineering therapy and/or animal breeding.

BRIEF DESCRIPTION OF THE FIGURES

FIG. 9 is a series of micrographs of tissue structures of teratoma from iPS cells.

DETAILED DESCRIPTION

Figure 1:
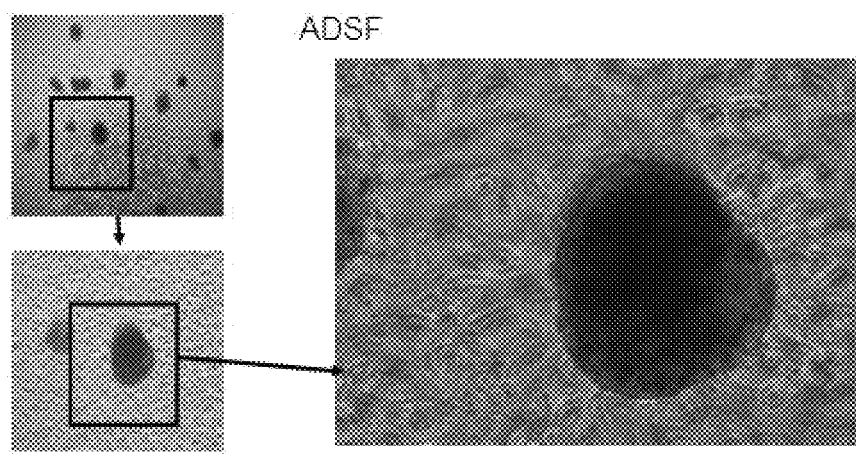
FIG. 1 is a micrograph showing human adult skin fibroblasts (ADSF) seeded on a hAEC feeder layer. Clones similar in appearance to ES cells were observed after 7 days.

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ansubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N.Y., 1987); and *Meth. Enzymol.*, Vols. 154 and 155, Wu & Grossman, and Wu, Eds., respectively. Methods to detect and measure levels of polypeptide gene expression products (i.e., gene translation level) are well-known in the art and include the use polypeptide detection methods such as antibody detection and quantification techniques. (See also, Strachan & Read, *Human Molecular Genetics*, Second Edition. (John Wiley and Sons, Inc., N.Y., 1999)).

Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or antigen-binding fragments thereof that specifically binds and recognizes an antigen. Use of the term antibody is meant to include whole antibodies, including single-chain whole antibodies. The term "antibody" includes bispecific antibodies and multispecific antibodies so long as they exhibit the desired biological activity or function.

As used herein, the term "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "feeder cells" refers to cells of one type that are co-cultured with cells of another type, to provide an environment in which the cells of the second type can grow. In some embodiments, somatic cells are co-cultured with feeder cells such as amniotic epithelial cells in order to reprogram the somatic cells into iPS cells.

As used herein, the term "gene" means a segment of DNA that contains all the information for the regulated biosynthesis of an RNA product, including promoters, exons, introns, and other untranslated regions that control expression.

As used herein, the term "isolated" means that materials naturally accompanying in normal circumstances are at least reduced, or preferably substantially completely eliminated. Therefore, the term "isolated cell" refers to a cell substantially free from other accompanying in natural circumstances substances (e.g., other cells, proteins, nucleic acids, etc.). The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized. Isolated nucleic acids are typically free from sequences naturally flanking the nucleic acid within an organism from which the nucleic acid is derived (i.e., sequences positioned at the 5' terminus and the 3' terminus of the nucleic acid).

As used herein the term "pluripotent stem cells" (PS cells) are cells that are capable under the right conditions of producing progeny of several different cell types. PS cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture. Included in the definition of PS cells are embryonic cells of various types, such as embryonic stem (ES) cells, as well as induced pluripotent stem cells (iPS) that have been reprogrammed from an adult somatic cell.

Those skilled in the art will appreciate that except where explicitly required otherwise, PS cells includes primary tissue and established lines that bear phenotypic characteristics of PS cells, and derivatives of such lines that still have the capacity of producing progeny of each of the three germ layers. PS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated PS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated PS cells, and may contain at least 40%, 60%, or 80% undifferentiated PS cells.

As used herein, the term "induced pluripotent stem cells" (abbreviated "iPS cells") refers to cells having properties similar to those of ES cells and encompasses undifferentiated cells artificially derived from a non-pluripotent cell, typically an adult somatic cell.

As used herein, the term "reprogramming" and grammatical equivalents refer to a process that alters or reverses the differentiation status of a somatic cell that is either partially or terminally differentiated. Reprogramming of a somatic cell may be a partial or complete reversion of the differentiation status of the somatic cell. In some embodiments, reprogramming is complete when a somatic cell is reprogrammed into an induced pluripotent stem cell. However, reprogramming may be partial, such as reversion into any less differentiated state. For example, reverting a terminally differentiated cell into a cell of a less differentiated state, such as a multipotent cell.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically-modified.

Overview

In one aspect, the present disclosure provides a method to obtain iPS cells. In some embodiments, the methods include culturing a somatic cell with a feeder layer of amniotic epithelial cells (AECs) for a sufficient time to dedifferentiate and reprogram the somatic cells.

In another aspect, the present disclosure provides iPS cells and the somatic cells differentiated from these iPS cells. The iPS cell can be a mammalian cell, for example a mouse, human, rat, bovine, ovine, horse, hamster, dog, guinea pig, or ape cell. For example, reprogramming of somatic cells provides an opportunity to generate patient- or disease-specific pluripotent stem cells. iPS cells are indistinguishable from ES cells in morphology, proliferation, gene expression, and teratoma formation. Furthermore, when transplanted into blastocysts, iPS cells can give rise to adult chimeras, which are competent for germline transmission (Maherali et al. *Cell Stem Cell* 1:55-70, 2007; Okita et al. *Nature* 448:313-17, 2007; Wernig et al. *Nature* 448:318-324, 2007). Human iPS cells are also expandable and indistinguishable from human embryonic stem (ES) cells in morphology and proliferation. Furthermore, these cells can differentiate into cell types of the three germ layers in vitro and in teratomas.

A first advantage of the present methods is that an iPS cell can be prepared from a somatic cell in the absence of eggs, embryos, or embryonic stem (ES) cells. A second advantage of the present methods is that iPS cell can be prepared from a somatic cell which was induced without an exogenous nucleic acid or/and chemical drugs. A third advantage of the present methods is that amniotic epithelial cells are used as a feeder and it is not necessary to treat these feeder cells with mitomycin C. Mitomycin C is a DNA damaging agent that could cause karyotypic changes in induced pluripotent cells. Consequently, using of mitomycin C may introduce a potential risk to future clinical applications. A fourth advantage of the present methods is that the methods possess following characteristics: simplicity of operation, good control and performance, low cost, high efficiency, and reproducibility.

Without wishing to be limited by theory, it is believed that the use of AEC feeder cells, or an extracellular matrix derived from the feeder cells, provides one or more substances necessary to induce pluripotency and promote the growth of the stem cells. Such substances are believed to include membrane-bound and/or soluble cell products that are secreted into the surrounding medium by the cells.

Preparation of AEC Cells

In one embodiment, amniotic epithelial cells (AEC) are used as a feeder layer for the culture of somatic cells, which induces the somatic cells to dedifferentiate into iPS cells, i.e. to become "reprogrammed". AECs develop from early inner cell masses of the blastula about 8 days after fertilization. The term "amnion" refers to fetus membrane, which is an important tissue for substance transport between maternal and fetal. AECs can be derived from mammals, such as humans, pigs, cattle, sheep, mice, and rats.

In a suitable embodiment, the AECs are human AECs (hAEC). hAECs can be obtained from human amnion. Known methods can also be used in further purification and enrichment of an active cell population by a person of ordinary skill in the art. Alternatively, the amniotic tissue may be dissected free of chorion and other placental tissues. The amnion layer may be gently stripped from the underlying chorion layer using forceps and a sterile scalpel. The amnion layer can be disaggregated mechanically and/or treated with digestive enzymes and/or chelating agents that weaken the connections between neighboring cells, making it possible to disperse the tissue suspension of individual cells. In yet another embodiment of the invention the chorion or decidua of the placenta can also be used as a source of AECs.

Enzymatic dissociation can be carried out by treating the amnion layer with any of a number of digestive enzymes. Such enzymes include, but are not limited to, trypsin, chymotrypsin, collagenase, elastase and/or hyaluronidase. In one embodiment, the isolated amniotic tissue is treated with trypsin to dissociate individual cells. In one embodiment, the concentration of trypsin for incubation of the tissue is about 0.05%. In one embodiment, the tissue is subjected to digestion with enzyme for varying periods of time, i.e., between 10 and 40 min, most suitably for 30 min. The tissue may also be subjected to multiple treatments with enzymes. A review of tissue disaggregation techniques is provided in, e.g., Freshney, Culture *of Animal Cells, A Manual of Basic Technique*, 2d Ed., A. R. Liss, Inc., New York, 1987, Ch. 9, pp. 107-126.

Following preparation of a single cell suspension, the cells can be cultured in medium containing a basal medium, supplemented with serum, hormones, growth factors, cytokines antibiotics, trace elements and other additives. Growth factors and cytokines may include fibroblast growth factors (FGFs), epidermal growth factor (EGF), transforming growth factor-β (TGF-β), hepatocyte growth factor (HGF) or oncostatin M. Additives to the medium may include insulin, transferrin, selenium (ITS), glucose, interleukin 6 and histone deacetylase inhibitors such as sodium butyrate or tricostatin A.

In one embodiment, amnion-derived cells are plated onto dishes with DMEM, 10% FBS, 2 mM L-glutamine, EGF (10 ng/ml), insulin (10 µg/ml), transferrin (5.5 µg/ml), selenium (6.7 ng/ml) and ethanolamine (2 µg/ml). In addition, sodium pyruvate and non-essential amino acids (1%) may be added to the culture medium. Those of skill in the art will also recognize that one or more commercially available substances may be used as additives or substitutions to the medium to support the growth of the AECs. The cells may be cryopreserved and retain function and viability when thawed.

The cells may be plated on tissue culture dishes or may be grown in a cell suspension in a flask, forming spheroidal cell bodies. When grown on tissue culture dishes, the surface may be coated electrostatically or with extracellular matrix components. Cells may be passaged before reaching confluency on the dish to avoid contact inhibition and maintain proliferating growth conditions.

Sources of Somatic Cells

The types of somatic cells that may be reprogrammed are not particularly limited, and any kind of somatic cells may be used. Mature somatic cells may be used, as well as somatic cells from an embryonic stage. Somatic cells may be primary cells or immortalized cells. Such cells may be primary cells (non-immortalized cells), such as those freshly isolated from an animal, or may be derived from a cell line (immortalized cells). In one embodiment, the somatic cells are mammalian cells, such as, for example, human cells or mouse cells. They may be obtained by well-known methods, from different organs, such as, but not limited to skin, lung, pancreas, liver, stomach, intestine, heart, reproductive organs, bladder, kidney, urethra and other urinary organs, or generally from any organ or tissue containing living somatic cells, or from blood cells. Mammalian somatic cells useful in the present invention include, by way of example, adult stem cells, lipocytes, mesenchymal cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Exemplary adult stem cells include hematopoietic stem cells, neural stem cells, and mesenchymal stem cells.

Methods for obtaining human somatic cells are well established, as described in, e.g., Schantz and Ng (2004), *A Manual for Primary Human Cell Culture*, World Scientific Publishing Co., Pte, Ltd. In some cases, the methods include obtaining a cellular sample, e.g., by a biopsy (e.g., a skin sample), blood draw, etc. Initial plating densities of cells prepared from a tissue may be varied based on such variables as expected viability or adherence of cells from that particular tissue. Methods for obtaining various types of human somatic cells include, but are not limited to, the following exemplary methods.

Bone Marrow.

The donor is given a general anesthetic and placed in a prone position. From the posterior border of the ilium, a collection needle is inserted directly into the skin and through the iliac surface to the bone marrow, and liquid from the bone marrow is aspirated into a syringe. The somatic stem cells are enriched by isolating bone marrow cells from an osteogenic zone of bone marrow. A mononuclear cell fraction is then prepared from the aspirate by density gradient centrifugation. The collected crude mononuclear cell fraction is then cultured prior to use in the methods described herein for reprogramming.

Skin Tissue.

Skin tissue containing the dermis is harvested, for example, from the back of a knee or buttock. The skin tissue is then incubated for 30 min at 37° C. in 0.6% trypsin/Dulbecco's Modified Eagle's Medium (DMEM)/F-12 with 1% antibiotics or antimycotics, with the inner side of the skin facing downward. After the skin tissue is turned over, tweezers are used to lightly scrub the inner side of the skin. The skin tissue is finely cut into 1 mm$^2$ sections using scissors and is then centrifuged at 1200 rpm and room temperature for 10 min. The supernatant is removed, and 25 ml of 0.1% t sin/DMEM/F-12/1% antibiotics or antimycotics, is added to the tissue precipitate. The mixture is stirred at 200-300 rpm using a stirrer at 37° C. for 40 min. After confirming that the tissue precipitate is fully digested, 3 ml fetal bovine serum (FBS) is added, and filtered sequentially with gauze, a 100 nm nylon filter and a 40 µm nylon filter. After centrifuging the resulting filtrate at 1200 rpm and room temperature for 10 min to remove the supernatant, DMEM/F-12/1% antibiotics or antimycotics is added to wash the precipitate, and then centrifuged at 1200 rpm and room temperature for 10 min. The cell fraction thus obtained is then cultured prior to reprogramming.

Epidermal stem cells can be enriched from human scalp tissues (0.5-2 cm$^2$ or less). Human scalp tissues are rinsed, trimmed to remove excess adipose tissues, and cut into small pieces. These tissue pieces are enzymatically digested in 12.5 mg/ml dispase (Invitrogen, Carlsbad, Calif.) in Dulbecco's modified Eagle's medium (DMEM) for 24 hours at 4° C. After the enzymatic treatment, the epidermis is peeled off from the dermis; and hair follicles are pulled out from the dermis. The bulb and intact outer root sheath (ORS) are dissected under the microscope. After the wash, the follicles are transferred into a plastic dish. Then the bulge region is dissected from the upper follicle using a fine needle. After the wash, the bulge is transferred into a new dish and cultured in medium containing DMEM/F12 and 10% FBS.

Skeletal Muscle.

The epidermis of a connective tissue containing muscle (such as the lateral head of the biceps brachii muscle or the sartorius muscle of the leg) is cut and the muscle tissue is excised. The whole muscle obtained is minced with scissors or a scalpel, and then suspended in DMEM (high glucose) containing 0.06% collagenase type IA and 10% FBS, and incubated at 37° C. for 2 hours. Cells are collected by centrifugation from the minced muscle, and suspended in DMEM (high glucose) containing 10% FBS. After passing the suspension through a microfilter with a pore size of 40 µm and then a microfilter with a pore size of 20 µm, the cell fraction obtained may be cultured as crude purified cells containing undifferentiated stem cells, and used for the induction of human pluripotent stem cells.

Adipose Tissue.

Cells derived from adipose tissue may be isolated by various methods known to a person skilled in the art. One source of adipose tissue is omental adipose tissue. In humans, adipose cells are typically isolated by fat aspiration. In one method of isolating cells, adipose tissue is treated with 0.01% to 0.5%, collagenase; 0.01% to 0.5%, trypsin; and/or 0.5 ng/ml to 10 ng/ml dispase, or an effective amount of hyaluronidase or DNase, and about 0.01 to about 2.0 mM EDTA at 25 to 50° C. for 10 min to 3 h. Cells are passed through nylon or a cheese cloth mesh filter of 20 μm to 800 μm. Then the cells in the culture medium are subjected to differential centrifugation directly or using Ficoll or Percoll or another particle gradient. The cells are centrifuged at 100 to 3000 g for 1 min to 1 h at 4 to 50° C. The adipose tissue-derived cell fraction thus obtained may be cultured according to the method described herein as crude purified cells containing undifferentiated stem cells, and used for the induction of human pluripotent or multipotent stem cells.

Blood. About 50 ml to about 500 ml vein blood or cord blood is collected, and a mononuclear cell fraction is obtained by the Ficoll-Hypaque method, as described in, e.g., Kanof et al., (1993), *Current Protocols in Immunology*, J. E. Coligan, A. M. Kruisbeek, D. H. Margulies, E. M. Shevack, and W. Strober, eds., ch. 7.1.1.-7.1.5, John Wiley & Sons, New York). After isolation of the mononuclear cell fraction, approximately $1 \times 10^7$ to $1 \times 10^8$ human peripheral blood mononuclear cells are suspended in a RPMI 1640 medium containing 10% fetal bovine serum, 100 μg/ml streptomycin and 100 units/ml penicillin, and after washing twice, the cells are recovered. The recovered cells are resuspended in RPMI 1640 medium and then plated in a 100 mm plastic petri dish at a density of about $1 \times 10^7$ cells/dish, and incubated in a 37° C. incubator at 8% $CO_2$. After 10 min, cells remaining in suspension are removed and adherent cells are harvested by pipetting. The resulting adherent mononuclear cell fraction is then cultured prior to reprogramming. In some cases, the peripheral blood-derived or cord blood-derived adherent cell fraction thus obtained may be cultured according to the method described herein as crude purified cells containing undifferentiated stem cells, and used for the induction of human pluripotent or multipotent stem cells.

Macrophages in the peripheral blood can be enriched by culturing the mononuclear cell fraction in low-glucose DMEM supplemented with 10% heat-inactivated fetal bovine serum (FBS; JRH Biosciences, Lenexa, Kans.), 2 mM L-glutamine, 50 U/ml penicillin, and 50 μg/ml streptomycin. In order to expand macrophages, peripheral blood mononuclear cells are spread at a density of $2 \times 10^6$/ml on plastic plates that have been treated with 10 μg/ml FN (Sigma, St. Louis, Mo.) overnight at 4° C. The cells are then cultured without any additional growth factors at 37° C. and 5% $CO_2$ in a humidified atmosphere. The medium containing floating cells is changed every 3 days. Macrophages with observable fibroblastic features may be used for reprogramming.

When iPS cells are used for therapeutic treatment of diseases, it is desirable to use somatic cells isolated from patients. For example, somatic cells involved in diseases, somatic cells participating in therapeutic treatment of diseases and the like can be used.

Reprogramming Somatic Cells to Obtain iPS Cells

In one aspect, the present invention provides methods for reprogramming and propagating somatic cells to produce iPS cells. iPS cultures can be obtained by passaging cells grown under feeder conditions, in which the feeder cells are amniotic epithelial cells (AECs). For instance, the somatic cells can be plated onto a AEC feeder layer in an appropriate medium, e.g., fetal bovine serum enhanced DMEM. The cells are cultured for about 2 to 14 days, typically about 7 days, or until the cells exhibit the morphological features of undifferentiated stem cells.

The culture medium used in the methods can be selected from conventional media for cell culture. Serum-containing medium is typically made with 80% DMEM, 20% defined fetal bovine serum (FBS), 1% non-essential amino acids, 1 mM L-glutamine, and 0.1 mM β-mercaptoethanol. The medium is filtered and stored at 4° C. for no longer than 2 weeks. Serum-free medium is made with 80% KO DMEM, 20% serum replacement (Gibco #10828-028), 1% non-essential amino acids, 1 mM L-glutamine, and 0.1 mM β-mercaptoethanol. Just before use, human bFGF may be added to a final concentration of 48 ng/mL. In one embodiment, DMEM medium with additional 10% fetal bovine serum, streptomycin, penicillin and glutamine is used. Optionally, human serum and/or umbilical serum can be added.

A method for selecting induced pluripotent stem cells that appear in a medium according to the method of the present invention is not particularly limited, and a well-known means may be suitably employed, for example, a drug resistance gene or the like can be used as a marker gene to isolate induced pluripotent stem cells using drug resistance as an index. Differentiation and proliferation abilities of isolated induced pluripotent stem cells can be easily confirmed by those skilled in the art by using confirmation means widely applied to ES cells.

iPS cells have the characteristic morphological features of undifferentiated stem cells. In the two dimensions of a standard microscopic image, iPS cells have high nuclear/cytoplasmic ratios in the plane of the image, prominent nucleoli, and compact colony formation with poorly discernible cell junctions. Cell lines can be karyotyped using a standard G-banding technique and compared to published human karyotypes. It is desirable to obtain iPS cells that have a "normal karyotype", which means that the cells are euploid, wherein all human chromosomes are present and are not noticeably altered. iPS cells can also be characterized by expressed cell markers detectable by antibody (flow cytometry or immunocytochemistry) or by reverse transcriptase PCR.

PCR can be used to detect marker gene expression. Induced pluripotent stem cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; .beta.III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tc11); DPPA3/Stella; DPPA4; other general markers for pluripotency, etc. Other markers can include Dnmt3L; Sox15; Stat3; Grb2; SV40 Large T Antigen; HPV16 E6; HPV16 E7, β-catenin, and Bmi1. Such cells can also be characterized by the down-regulation of markers characteristic of the differentiated cell from which the iPS cell is induced. For example, iPS cells derived from fibroblasts may be characterized by down-regulation of the fibroblast cell marker Thy1 and/or up-regulation of SSEA-1. It is understood that the present invention is not limited to those markers listed herein, and encompasses markers such as cell surface markers, antigens, and other gene products including ESTs, RNA (including microRNAs and antisense RNA), DNA (including genes and cDNAs), and portions thereof. Those colonies which show expression of these markers can then be used in further therapeutic applications or stored.

Another desirable feature of propagated iPS cells is a potential to differentiate into cells of all three germ layers: endoderm, mesoderm, and ectoderm. Pluripotency of iPS cells can be confirmed by forming teratomas in SCID mice, and examining them for representative tissues of all three germ layers. Alternatively, pluripotency can be determined by allowing iPS cells to differentiate non-specifically (for example, by forming embryoid bodies), and then determining the cell types represented in the culture by immunocytochemistry.

Certain iPS cell populations described herein are substantially undifferentiated, and can be passaged between multiple cultures in the conditions described. During passage, some cells may differentiate (particularly when replated as single cells at low density, or when large clusters are allowed to form). However, cultures typically reestablish a larger proportion of undifferentiated cells as they reapproach confluence.

Genetic Alteration of Pluripotent Stem Cells

This disclosure also provides a system for obtaining iPS cells that have been genetically altered, either in a transient or stable fashion. The cells may be modified to give them desired properties in the undifferentiated state, to give them desired properties after differentiation into other cell types, or to provide a method to positively or negatively select for particular undifferentiated or differentiated phenotypes.

For therapeutic applications, it may be beneficial to modify cells with therapeutic genes, or to render cells histocompatible with the intended recipient. Genetic alteration can also be used to prepare cells for sorting after differentiation. For example, the iPS cells are transfected with a drug susceptibility gene, such as herpes simplex virus thymidine kinase (which renders cells susceptible to ganciclovir), under control of a promoter specific for undifferentiated cells, such as the OCT-4 promoter or the hTERT promoter. After the culture has been made to differentiate, residual undifferentiated cells can be eliminated from the population using ganciclovir.

Suitable vector plasmids for transfecting into iPS cells include lipid/DNA complexes, such as those described in U.S. Pat. Nos. 5,578,475; 6,020,202; and 6,051,429. Suitable reagents for making DNA-lipid complexes include lipofectamine (Gibco/Life Technologies #11668019) and FuGENE™ (Roche Diagnostics Corp. #1814443); and Lipo-TAXI™ (Invitrogen Corp., #204110). Viral vector systems for producing iPS cells with stable genetic alterations can be based on adenovirus, retrovirus, or lentivirus, prepared using commercially available virus components. Genetic alteration of iPS cells requires achieving sufficiently high efficiency of genetic alteration, while not promoting differentiation of the iPS cells along an undesired pathway.

Following genetic alteration and drug selection (on drug-resistant feeders or feeder-free culture), it is possible to pick colonies that demonstrate the altered phenotype, and culture them separately. The picked colonies are dispersed into small clumps of 25-100 cells, and replated in a suitable environment. It is possible to achieve cultures of pPS cells in which a high proportion (up to 90%) of the undifferentiated cells are genetically altered.

Uses of Propagated iPS Cells

The present disclosure provides iPS cells produced using the methods described herein, as well as populations of such cells. The reprogrammed cells, capable of differentiation into many cell types, have a variety of applications and therapeutic uses. The basic properties of stem cells, i.e., the capability to infinitely self-renew and the ability to differentiate into every cell type in the body, make them ideal for therapeutic uses.

Accordingly, in one aspect the present invention further provides a method of treatment or prevention of a disorder and/or condition in a subject using iPS cells generated from the methods described herein. The method includes obtaining a somatic cell from a subject and reprogramming the somatic cell into an iPS cell. The cell is then cultured under suitable conditions to differentiate the cell into a desired cell type suitable for treating the condition. The differentiated cell may then be introduced into the subject to treat or prevent the condition.

The iPS cells can be tailored specifically to the patient, avoiding immune rejection. Therefore, it will obviate the significant problem associated with current transplantation methods, such as, rejection of the transplanted tissue which may occur because of host versus graft or graft versus host rejection. For example, use of iPS cells in bone marrow transplants, will circumvent the requirement of providing heavy immune suppression with drugs that have potentially adverse side effects.

The iPS cells may be differentiated into a number of different cell types to treat a variety of disorders by methods known in the art. For example, iPS cells may be induced to differentiate into hematopoetic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition. For example, if cells of the neural lineage are desired, iPS cells are changed to a culture medium containing one or more neurotrophins (such as neurotrophin 3 or brain-derived neurotrophic factor) and one or more mitogens (such as epidermal growth factor, basic fibroblast growth factor, platelet-derived growth factor, insulin-like growth factor 1, and erythropoietin). Cultured cells are optionally separated based on whether they express a marker such as A2B5 or NCAM. Neural precursors can be obtained having the capacity to generate both neuronal cells (including mature neurons), and glial cells (including astrocytes and oligodendrocytes). Alternatively, replicative neuronal precursors can be obtained that have the capacity to form differentiated cell populations in which at least 5% of all the cells in the population express tyrosine hydroxylase, a marker of dopaminergic neurons. If cells of the hepatocyte lineage are desired, then iPS cells may be cultured in the presence of a histone deacetylase inhibitor such as n-butyrate. The cultured cells are optionally cultured simultaneously or sequentially with a hepatocyte maturation factor, such as EGF, insulin, and FGF. If cells expressing characteristic markers of cardiomyocytes are desired, differentiation is facilitated by nucleotide analogs that affect DNA methylation (such as 5-aza-deoxy-cytidine), growth factors, and bone morphogenic proteins. The cells can be further enriched by density-based cell separation, and maintained in media containing creatine, carnitine, and taurine.

The methods of the present invention can also be used in the treatment or prevention of neurological diseases. Such diseases include, for example, Alzheimer's disease, Parkinson's disease, Huntington's disease, amyotrophic lateral sclerosis (ALS), lysosomal storage diseases, multiple sclerosis, spinal cord injuries and the like. The methods of the present invention can also be used to correct mutations of single genes. These mutations account for diseases such as cystic fibrosis, hemophilia, and various cancers such as those associated with the BRCA1 and BRCA2 mutations with high risk of development of breast and ovarian cancers.

The cells produced in the methods of the invention can be utilized for repairing or regenerating a tissue or differentiated cell lineage in a subject. The method includes obtaining the reprogrammed cell as described herein and administering the cell to a subject (e.g., a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, and genetic disorders) and similar diseases, where an increase or replacement of a particular cell type/tissue or cellular de-differentiation is desirable. In one embodiment, the subject has damage to the tissue or organ, and the administering provides a dose of cells sufficient to increase a biological function of the tissue or organ or to increase the number of cell present in the tissue or organ. In another embodiment, the subject has a disease, disorder, or condition, and wherein the administering provides a dose of cells sufficient to ameliorate or stabilize the disease, disorder, or condition. In yet another embodiment, the subject has a deficiency of a particular cell type, such as a circulating blood cell type and wherein the administering restores such circulating blood cells.

Differentiated cells of this invention can also be used for tissue reconstitution or regeneration in a human patient in need thereof. The cells are administered in a manner that permits them to graft to the intended tissue site and reconstitute or regenerate the functionally deficient area.

In one example, neural stem cells are transplanted directly into parenchymal or intrathecal sites of the central nervous system, according to the disease being treated. Grafts are done using single cell suspension or small aggregates at a density of 25,000 500,000 cells per μL (U.S. Pat. No. 5,968, 829). The efficacy of neural cell transplants can be assessed in a rat model for acutely injured spinal cord as described by McDonald et al. (*Nat. Med.* 5:1410, 1999), and Kim et al. (*Nature* 418:50, 2002). A successful transplant will show transplant-derived cells present in the lesion 2-5 weeks later, differentiated into astrocytes, oligodendrocytes, and/or neurons, and migrating along the cord from the lesioned end, and an improvement in gait, coordination, and weight-bearing.

The efficacy of cardiomyocytes can be assessed in an animal model for cardiac cryoinjury, which causes 55% of the left ventricular wall tissue to become scar tissue without treatment (Li et al., *Ann. Thorac. Surg.* 62:654, 1996; Sakai et al., *Ann. Thorac. Surg.* 8:2074, 1999, Sakai et al., *J. Thorac. Cardiovasc. Surg.* 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., *Cell Transplant.* 7:239, 1998), or by ligation of the left anterior descending coronary artery (Min et al., *J. Appl. Physiol.* 92:288, 2002). Efficacy of treatment can be evaluated by histology and cardiac function. Cardiomyocyte preparations embodied in this invention can be used in therapy to regenerate cardiac muscle and treat insufficient cardiac function (U.S. Pat. No. 5,919,449 and WO 99/03973).

Hepatocytes and hepatocyte precursors can be assessed in animal models for ability to repair liver damage. One such example is damage caused by intraperitoneal injection of D-galactosamine (Dabeva et al., *Am. J. Pathol.,* 143:1606, 1993). Efficacy of treatment can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

For purposes of commercial distribution, cells prepared according to this invention are typically supplied in the form of a pharmaceutical composition comprising an isotonic excipient, and prepared under conditions that are sufficiently sterile for human administration. For general principles in medicinal formulation of cell compositions, see *Cell Therapy: Stem Cell Transplantation, Gene Therapy, and Cellular Immunotherapy*, by G. Morstyn & W. Sheridan eds, Cambridge University Press, 1996; and Hematopoietic Stem Cell Therapy, E. D. Ball, J. Lister & P. Law, Churchill Livingstone, 2000. The cells may be packaged in a device or container suitable for distribution or clinical use, optionally accompanied by information relating to use of the cells in tissue regeneration, or restoring a therapeutically important metabolic function.

EXAMPLES

The following Examples are presented in order to more fully illustrate some embodiments of the invention. These Examples should in no way be construed as limiting the scope of the invention, as defined by the appended claims.

Example 1

Preparation of Human Amniotic Epithelial Cells

This example describes the preparation of human amniotic epithelial cells (hAECs). The amniotic membrane of placentas delivered by elective cesarean section was dissected from the fetal membranes. The underlining sponge layer and fibrous tissue were removed to obtain a layer of amniotic cells with the basement membrane zone (BMZ) lying beneath the stratified epithelium. Next, then amniotic cells were isolated from the membrane. The membrane was cut into pieces and placed in a 250 ml flask with RPMI 1640 medium. The cells were digested with 0.25% trypsin/EDTA for 30 min, and a second time for 15 min. The cells were collected by centrifugation and seeded in 6-well plates. The cells were grown in DMEM medium+10% FBS (PAA Austria) and antibiotics generally used in cell culture, and incubated at 37° C., 5% $CO_2$.

Example 2

Isolation of Human Adult Skin Fibroblasts (ADSF)

This example describes the preparation of human adult skin fibroblasts (ADSF). Human skin or scar tissue containing ADSF cells was isolated and placed in cold PBS. The skin was cut into pieces of approximately 1 $mm^2$ and incubated with PBS containing 0.25% trypsin+0.2 mg/ml DNaseI) at 37° C. for 30 min, and then neutralized with DMEM containing 15% heat-inactivated horse serum. The cell concentration was adjusted to approximately $1 \times 10^6$/mL and seeded into 6-well plates. The cells were incubated at 37° C., 5% $CO_2$.

Example 3

Isolation of Mouse Fibroblasts

This example describes the isolation of mouse fibroblasts. Under aseptic conditions, tissue collected from a mouse ear was cut into pieces of approximately 1 $mm^3$. The tissue was washed with PBS twice and placed in DMEM medium, in 6-well plates overnight. The next day, 2 ml of medium was added and the culture was continued until approximately 90% of plates were covered with cells. The cells were incubated at 37° C., 5% $CO_2$.

Example 4

Isolation of Pig Embryonic Fibroblasts

This example describes the isolation of pig embryonic fibroblasts. Under aseptic conditions, a pig embryo was washed with PBS 2-3 times. The head and viscera were discarded and the remaining embryo tissue was cut into pieces of about 1 $mm^3$, and washed with PBS twice to remove blood cells. DMEM medium was added and the tissue was incubated overnight at 37° C., 5% $CO_2$. Six (6) ml of medium was added the next day and the culture was continued until approximately 90% of plate was covered.

Example 5

Preparation of ADSF-Derived Pluripotent Stem Cells

ADSF provided by International Peace Maternity and Children's Hospital of the China Welfare Institute were prepared as described in Example 2. The cells were cultured with a hAEC feeder layer in KO-DMEM medium (10 ng/ml bFGF, 5% human umbilical serum, 12 ng/ml hLIF). The cell status was observed throughout the incubation process. The cells were incubated at 37° C., 5% $CO_2$. The results are shown in FIG. 1. Clones exhibited a similar appearance to ES cell after 7 d of culture.

Example 6

Preparation of Mouse Fibroblast-Derived Pluripotent Stem Cells

Figure 5:
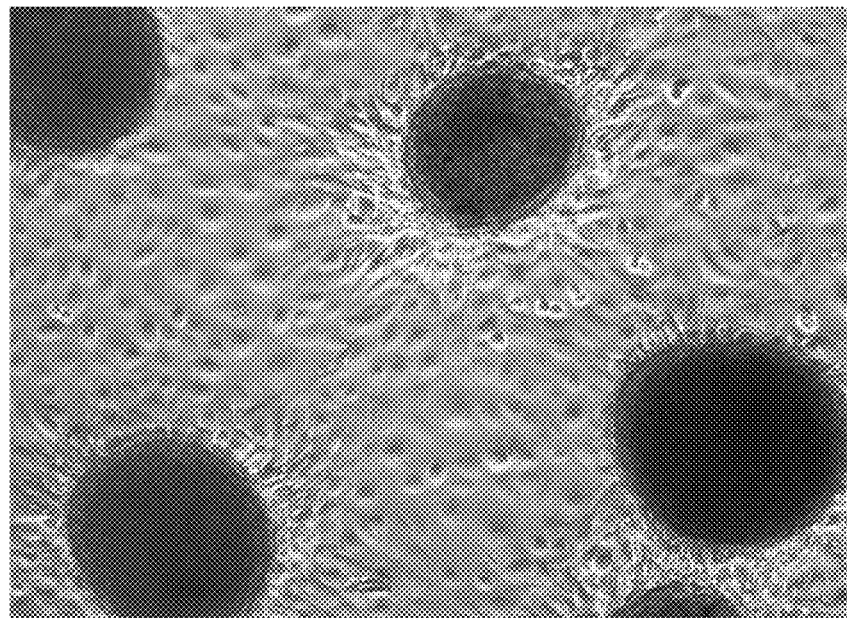
FIG. 5 is a micrograph showing mouse fibroblast (MF) cells seeded on a hAEC feeder layer. Clones similar in appearance to ES cells were observed after 3 days.

Mouse fibroblasts were prepared as described in Example 2. The cells were cultured with a hAEC feeder layer in KO-DMEM medium (10 ng/ml bFGF, 5% human umbilical serum, 12 ng/ml hLIF). The cell status was observed throughout the incubation process. The cells were incubated at 37° C., 5% $CO_2$. The results are shown in FIG. 5. Clones exhibited a similar appearance to ES cell after 3 d of culture.

Example 7

Preparation of Pig Embryonic Fibroblast-Derived Pluripotent Stem Cells

Figure 7:
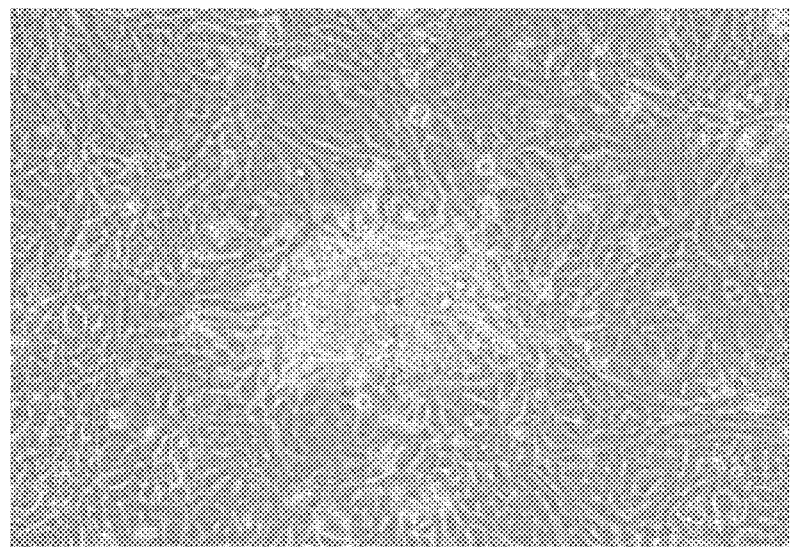
FIG. 7 is a micrograph showing pig embryonic fibroblast (PEF) cells seeded on a hAEC feeder layer.

Pig embryonic fibroblasts were prepared as described in Example 2. The cells were cultured with a hAEC feeder layer in KO-DMEM medium (10 ng/ml bFGF, 5% human umbilical serum, 12 ng/ml hLIF). The cell status was observed throughout the incubation process. The cells were incubated at 37° C., 5% $CO_2$, 5% $O_2$. The results are shown in FIG. 7. Clones exhibited a similar appearance to ES cell after 5-7 d of culture.

Example 8

Immunofluorescence Assay

Figure 2A:
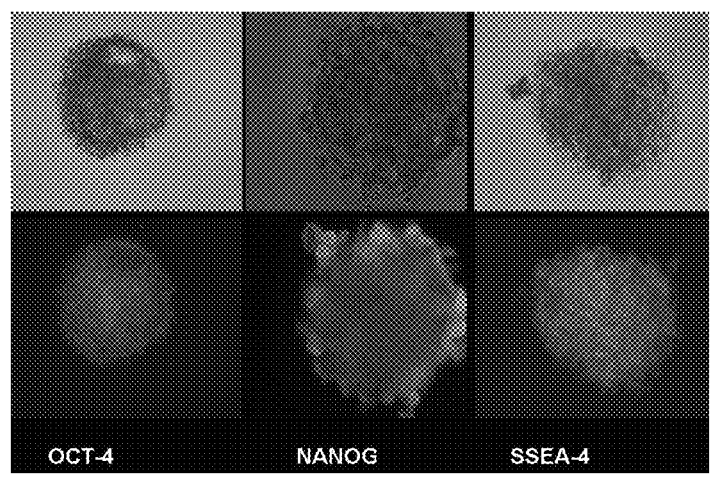
FIGS. 2A-2B are a series of micrographs showing staining of stem cell markers in clones from ADSF cells cultured for 7 days on a hAEC feeder layer. The cells expressed OCT-4, NANOG, SSEA-4, KLF-4, C-MYC, TAR-81, and TAR-60, which are stem cell specific makers.
Figure 2B:
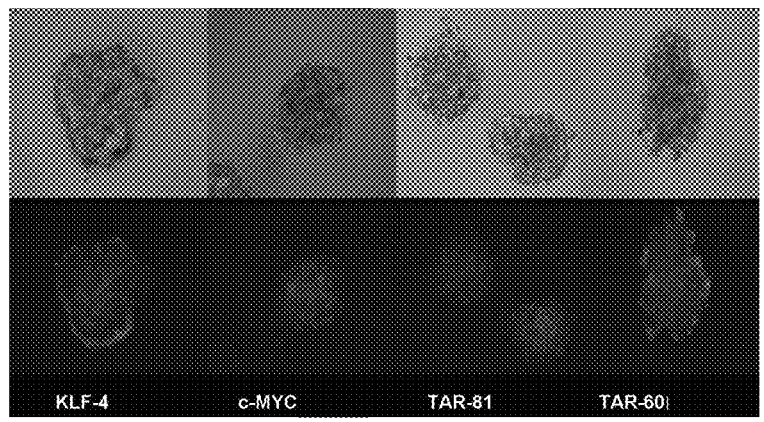
Figure 6:
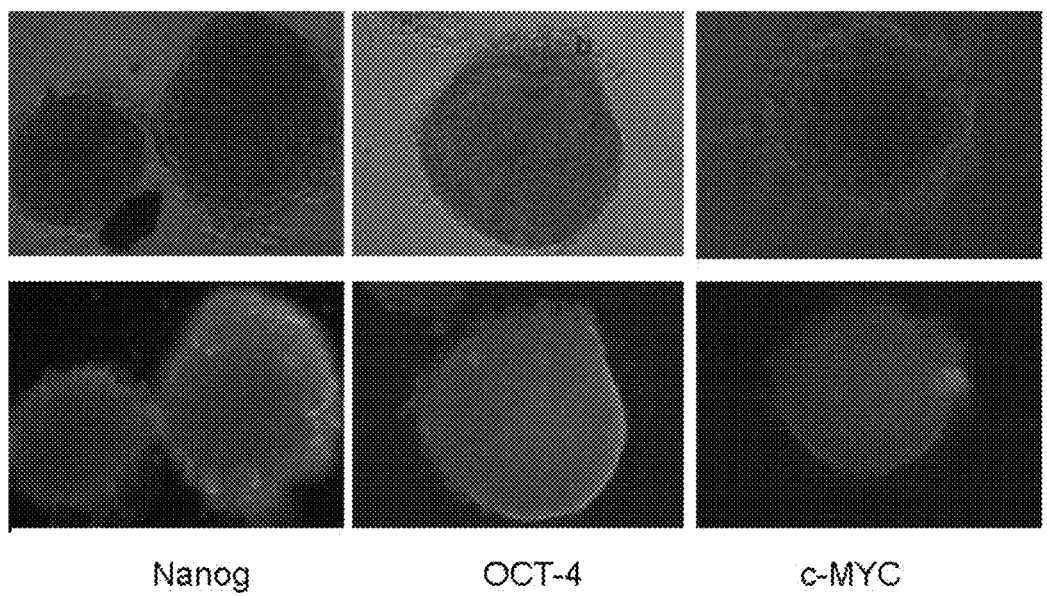
FIG. 6 is a series of micrographs showing staining of stem cell markers in clones from MF cells cultured for 3 days on a hAEC feeder layer.

This example describes the analysis of iPS cells for stem cell marker gene expression using immunofluorescence. Cells were washed with PBS 3 times and fixed with 2% paraformaldehyde at room temperature. The cells were washed with PBS 3 times (5 min each) and permeabilized with 0.1% Triton X-100 for 15 min. Next, the cells were washed with PBS 3 times (5 min each) and blocked with 5% BSA at RT for 2 h. Primary antibodies for SSEA-4, Nanog, Oct-4 were added and incubated overnight. The cells were washed with PBS 3 times (5 min each), and then labelled with secondary antibody at RT for 1 h. The cells were incubated with Hochest dye (1:1000) at RT in a dark place. The positive cells were observed after glycerol gangliolysis. The results from analysis of ADSF-iPS cells are shown in FIG. 2 and indicate positive stem cell marker staining in the ADSF-iPS cells. The results from analysis of MF-iPS cells are shown in FIG. 6.

Example 9

Gene Expression Assay by q-PCR

This example describes the analysis of iPS cells for stem cell marker gene expression using RT-PCR. Extraction of mRNA and RT-PCR was performed according to the manufacturer's instructions (Promega, AS-1050). The PCR primers used for each of the marker genes are shown in Table 1. cDNA of each group of cells was used as the template for realtime-PCR on an Eppendorf RealPlex instrument. The RT-PCR was performed using two-step method, and the amplification rate of the target fragment was calculated by relative quantitative method to the amount of 18s rRNA.

TABLE 1

PCR Primers for Detecting Stem Cell Markers

| Target | Forward Primer | Reverse Primer | Amplicon Size (bp) |
|---|---|---|---|
| Oct-4 | GAGGAGTCCCAGGACATGAA (SEQ ID NO: 1) | GTGGTCTGGCTGAACACCTT (SEQ ID NO: 2) | 151 |
| Sox-2 | GCCGAGTGGAAACTTTTGTC (SEQ ID NO: 3) | GTTCATGTGCGCGTAACTGT (SEQ ID NO: 4) | 264 |
| Rex-1 | GCGTACGCAAATTAAAGTCCAGA (SEQ ID NO: 5) | CAGCATCCTAAACAGCTCGCAGAAT (SEQ ID NO: 6) | 306 |
| TERT | AGAGTGTCTGGAGCAAGTTGC (SEQ ID NO: 7) | CGTAGTCCATGTTCACAATCG (SEQ ID NO: 8) | 185 |

TABLE 1-continued

PCR Primers for Detecting Stem Cell Markers

| Target | Forward Primer | Reverse Primer | Amplicon Size (bp) |
|---|---|---|---|
| Nanog | CTCAGCCTCCAGCAGATGC (SEQ ID NO: 9) | CCTTCTGCGTCACACTG (SEQ ID NO: 10) | 150 |
| 18s rRNA | CCCCAGCCCTCTCCTCCCCAATA (SEQ ID NO: 11) | TGCCCCCCACCCTCCCACAGTAG (SEQ ID NO: 12) | 190 |

Figure 3A:
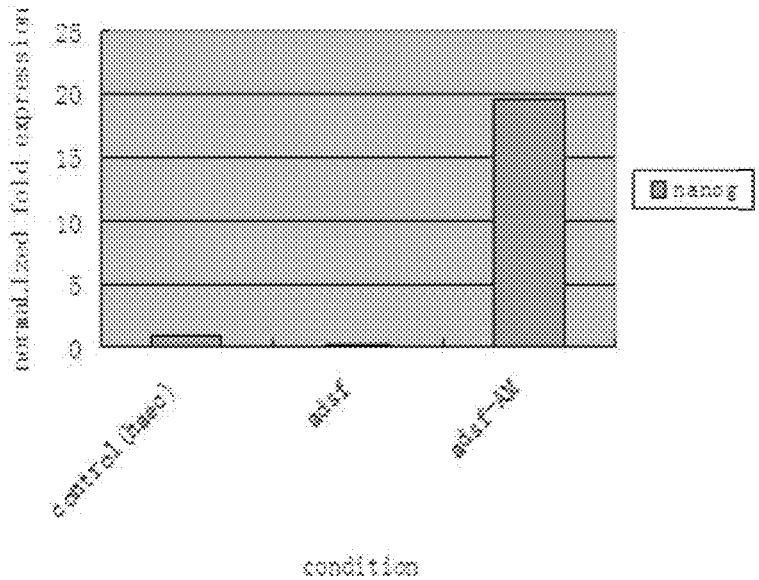
FIG. 3A-3C are charts showing the quantitative expression of markers in ADSF-iPS cells (7 days).
Figure 3B:
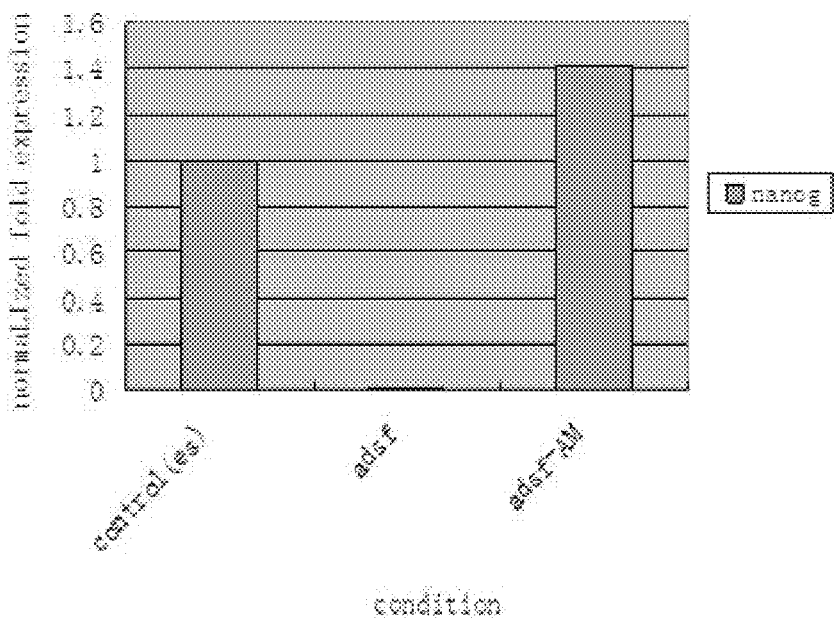
Figure 3C:
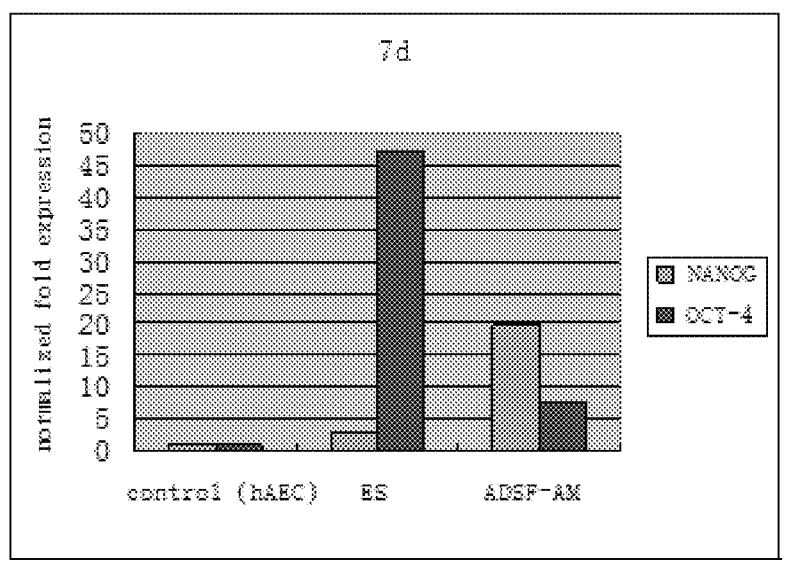
Figure 4A:
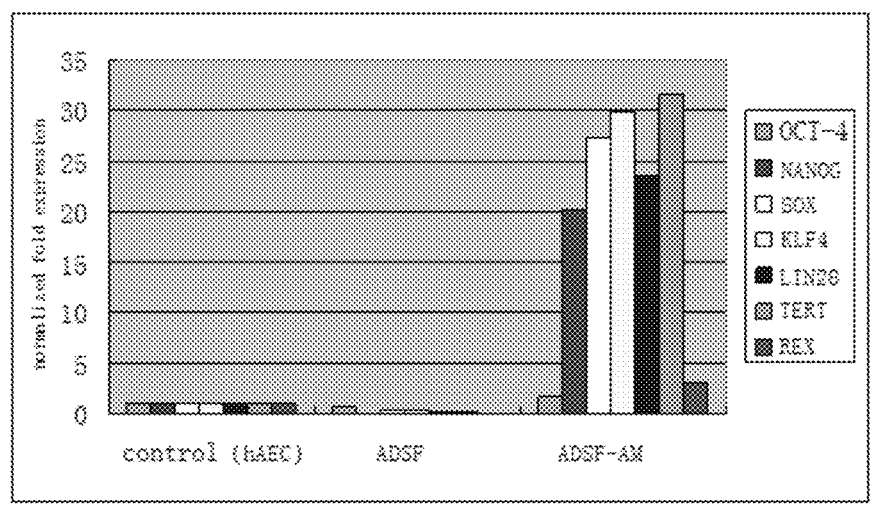
FIG. 4A-4C are charts showing the quantitative expression of stem cell markers in various cell types after 12 days of culture.
Figure 4B:
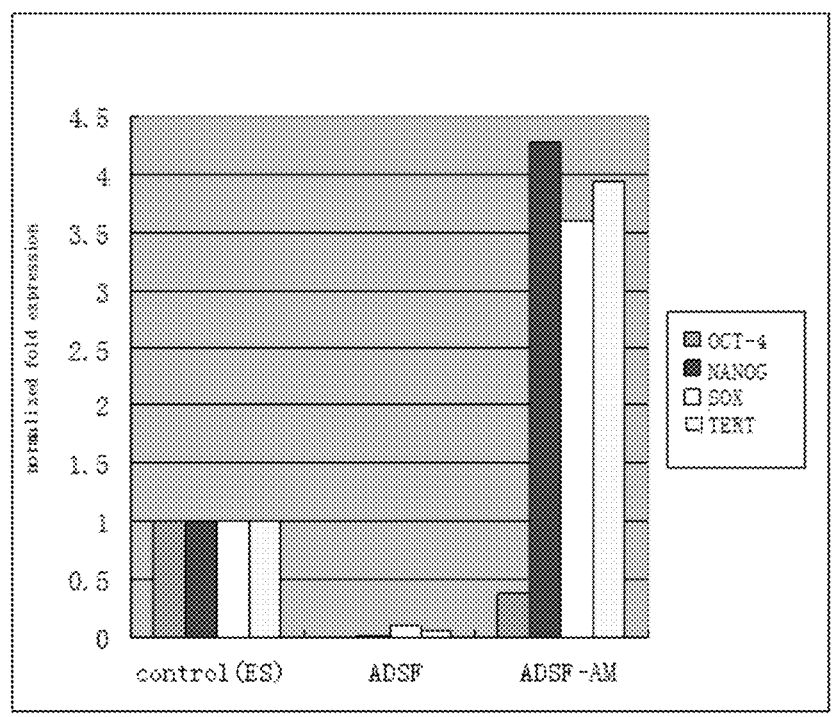
Figure 4C:
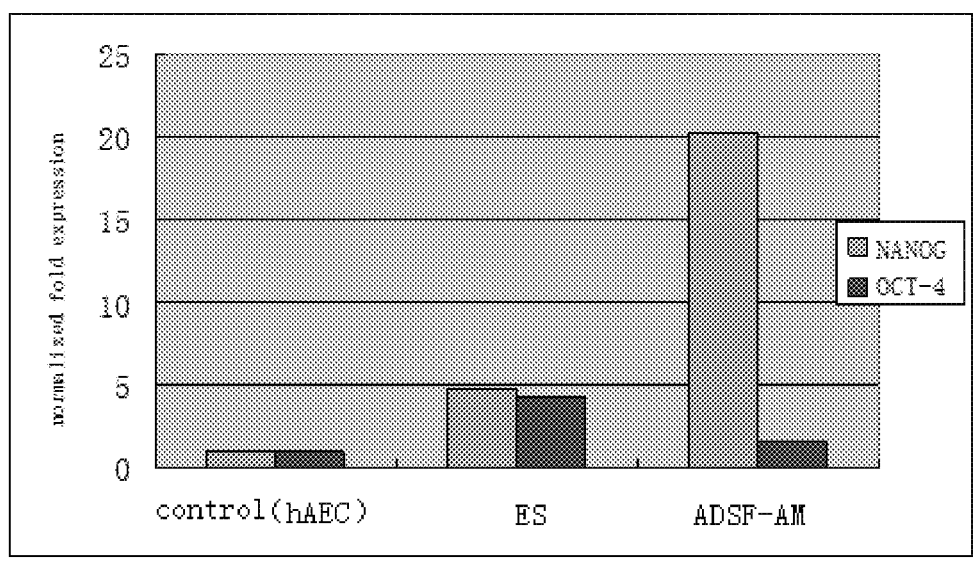

The results of the analysis of marker gene expression in iPS cells is shown in FIGS. 3 and 4. Data are expressed as percentage of control by normalization. The expression of NANOG, SOX-2, KLF-4, LIN28, TERT were more than 20 fold higher in ADSF-iPS compared with that of hAEC. These stem cell marker (NANOG, SOX-2, KLF-4, TERT) expression of iPS cells was higher than ES, but expression of OCT-4 was lower. For ADSF, there is little expression of stem cell markers.

Example 10

Identification of the Centromeres of Chromosomes from Mouse iPS Cells

Preparation of Cells.

$1 \times 10^6$ pluripotent cells derived from mouse fibroblasts were seeded onto a 100 mm dish. After 48-h of culture, the culture medium was changed (5 mL) and incubated overnight. Next, 70 ng/mL colchicine was added and the culture was continued 5 h. The cells were harvested and treated with 75 mM KCl for 10-20 min and fixed with methanol/acetic acid (3:1 vol/vol) to obtain the cell suspensions.

Primed In Situ (PRINS) Labeling.

In order to image the chromosomes, fixed metaphase cells were dropped onto slides and aged for 1-4 days. Next, the slides were denatured with deionized formamide for 2 min and dehydrated with an ethanol series (70, 90 and 100%). After the slides were air-dried, the following components were added: buffer (20 µl), glycerol (10 µl), dNTP-dig (5 µl), forward and reverse primers (5 µl), 5 µl Taq polymerase, and deionized water (158 µl). The sequences of the primers were: Major satDNA: 5'-GGACCTGGAATATGGCGAGAAA-3' (SEQ ID NO: 13); and Minor satDNA: 5'-TGATATACACT-GTTCTACAAATCCCG-3' (SEQ ID NO: 14).

The primers were allowed to anneal for 10 min, and then the temperature was raised to 72° C. for 12 min for elongation. The slides were then washed with NE solution for 5 min at 72° C. and 4 times with SSC/0.5% Tween-20 for 5 min. The slides were dried and an anti-Digoxin-labeled antibody was added and incubated at 37° C. for 30 min. The slides were washed with PBS/0.2% Tween-20 for 5 min and air-dried. Finally, DAPI was added the cells were observed under a fluorescent microscope.

Figure 8:
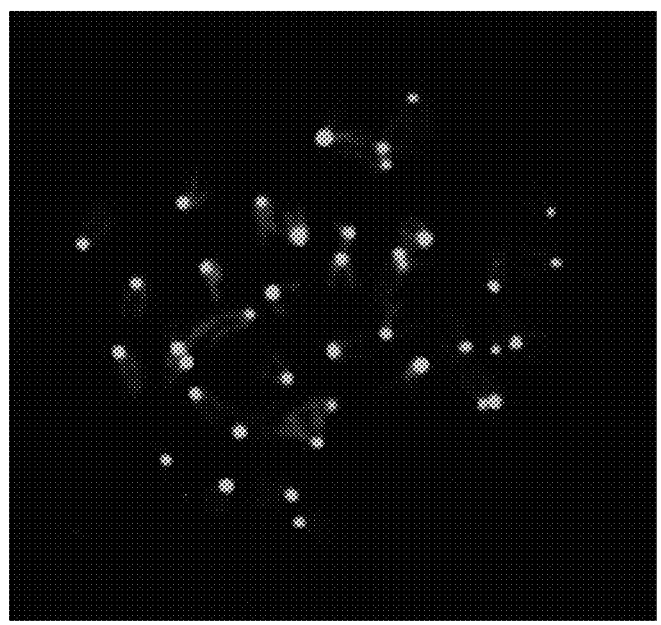
FIG. 8 is a micrograph showing the centromeres labeled with anti-Digoxin labeled antibody of mouse chromosomes The observed centromere located on the top of chromosome, indicated that there was no occurrence of hAEC chromosome contamination. Karyotype analysis: iPS cells with normal diploid karyotype of mouse, a total of 40 chromosomes.

The results are shown as FIG. 8. The observed centromere located on the top of chromosome indicates that the chromosomes were derived from mouse, and further indicated that there was no occurrence of hAEC chromosome contamination. Karyotype analysis showed that the iPS cells had a normal diploid karyotype, i.e., a total of 40 chromosomes.

Example 11

Teratoma Formation of the Induced Pluripotent Cells

Figure 9A:
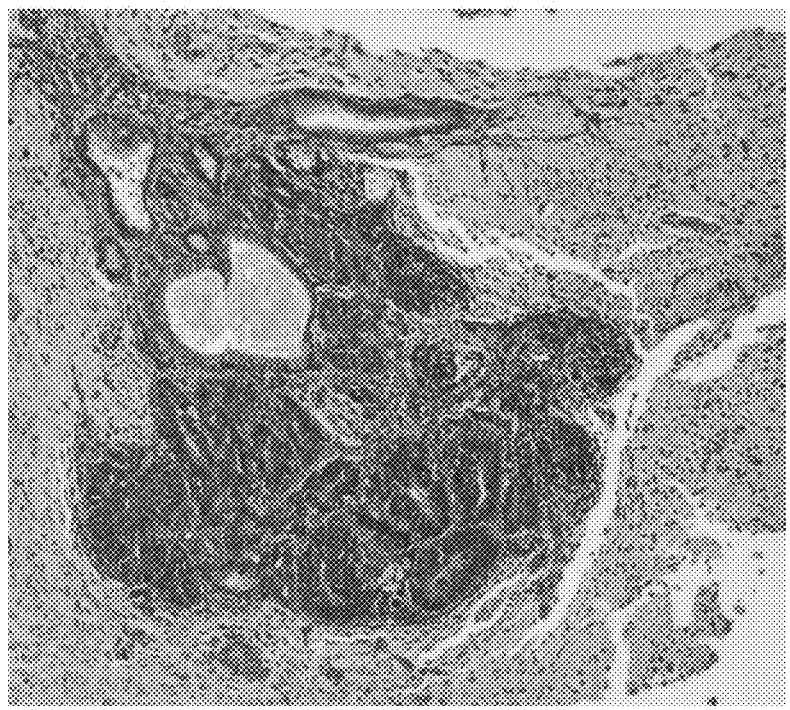
FIG. 9A shows glandular tissue (endoderm)
Figure 9B:
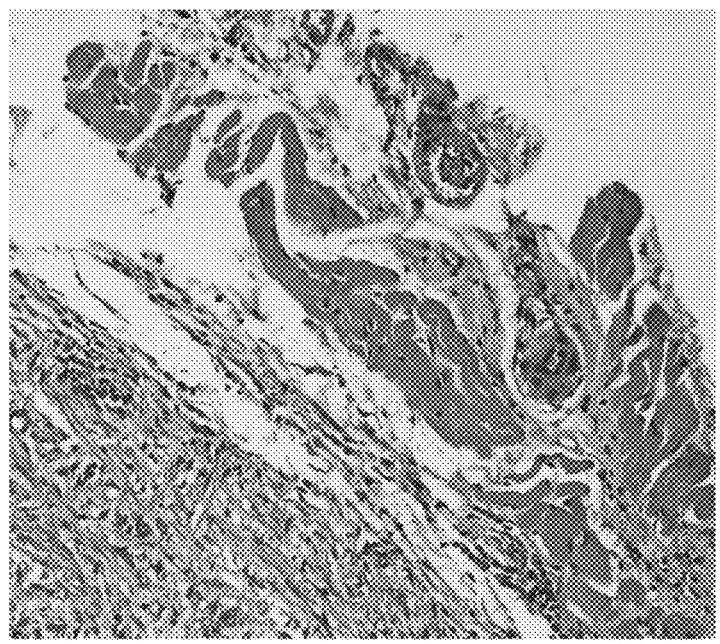
FIG. 9B shows musculature (mesoderm)
Figure 9C:
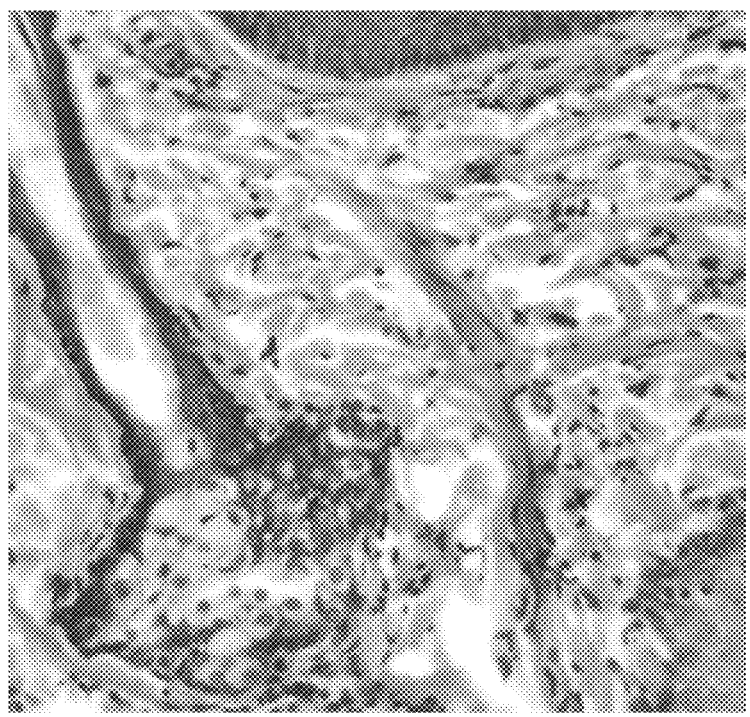
FIG. 9C shows skin tissue (ectoderm).

In this Example, the ability of iPS cells to form teratomas was examined. iPS cells were derived from mouse skin fibroblasts induced with human amniotic epithelial cells To test pluripotency of the induced pluripotent cells in vivo, the cells were transplanted subcutaneously into dorsal flanks of immunodeficient nude mice. Eight weeks after injection, tumor formation was observed. The examination showed that the tumor contained various tissues (FIG. 9), including glandular tissue (endoderm), musculature (mesoderm), skin tissue (ectoderm). The tissue structures of the teratoma demonstrated that the iPS cells have the ability for developmental pluripotency.

The results of these examples demonstrates that human adult skin fibroblasts with hAEC as a feeder layer can be induced into a stem cell-like clone under the appropriate culture conditions. These clones had high expression of stem cell markers. The ADSF clones induced by hAEC emerged earlier than iPS cells that are generated by routine methods (i.e., transfecting cells with Oct4, Sox2, c-Myc, Klf4 for 2 weeks (mouse iPS) or 4 weeks (human iPS). Moreover, the quantity of cells obtained in clusters was much greater than that obtained from routine methods. As such, the present methods are useful to generate iPS cells from adult somatic tissues.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for obtaining human induced pluripotent stem cells comprising culturing human adult skin fibroblast cells on a feeder layer of human amniotic epithelial cells for a period of time sufficient to reprogram the adult skin fibroblast cells into human induced pluripotent stem (iPS) cells.

2. The method of claim 1, wherein the amniotic epithelial cells have been cultured for fewer than 6 serial passages ($P_0$-$P_5$).

3. The method of claim 2, wherein the amniotic epithelial cells are newly isolated $P_0$ amniotic epithelial cells.

4. The method of claim 1, wherein the amniotic epithelial cells are cultured in KO-DMEM medium.

5. The method of claim 4, wherein the KO-DMEM medium comprises basic fibroblast growth factor (bFGF), human umbilical serum, newborn bovine serum, fetus bovine serum and Leukemia Inhibitor Factor (LIF).

6. The method of claim 5, wherein the KO-DMEM comprises 10 ng/ml bFGF, 5% human umbilical serum and 12 ng/ml LIF.

7. The method of claim 1, wherein the human iPS cells express at least one stem cell-specific marker selected from the group consisting of Oct-4, Sox-2, Rex-1, telomerase reverse transcriptase (TERT), Nanog, LIN28, SSEA-4, KLF-4, and C-MYC.

* * * * *